United States Patent [19]

Kwiatkowski et al.

[11] Patent Number: 4,931,219

[45] Date of Patent: Jun. 5, 1990

[54] PHOTOCHROMIC COMPOUND AND ARTICLES CONTAINING THE SAME

[75] Inventors: Patricia L. Kwiatkowski; Won S. Kwak, both of Akron, Ohio

[73] Assignee: PPG Industries, Inc., Pittsburgh, Pa.

[21] Appl. No.: 366,230

[22] Filed: Jun. 12, 1989

Related U.S. Application Data

[63] Continuation of Ser. No. 78,325, Jul. 27, 1987, abandoned.

[51] Int. Cl.$^5$ .............................................. G02B 5/23
[52] U.S. Cl. ..................................... 252/586; 544/70; 544/71; 350/354
[58] Field of Search ..................... 252/586; 544/70, 71

[56] References Cited

U.S. PATENT DOCUMENTS

| | | | |
|---|---|---|---|
| 3,562,172 | 2/1971 | Ono et al. | 252/600 |
| 3,578,602 | 5/1971 | Ono et al. | 252/600 |
| 4,215,010 | 7/1980 | Hovey et al. | 252/586 |
| 4,342,668 | 8/1982 | Hovey et al. | 252/586 |
| 4,637,698 | 1/1987 | Kwak et al. | 351/163 |
| 4,719,296 | 1/1988 | Irie | 544/71 |

FOREIGN PATENT DOCUMENTS

| | | | |
|---|---|---|---|
| 62-155283 | 7/1987 | Japan | 544/71 |
| 62-195075 | 8/1987 | Japan | 544/71 |
| 62-195383 | 8/1987 | Japan. | |
| 2171404 | 8/1986 | United Kingdom. | |
| 85/02619 | 12/1983 | World Int. Prop. O. . | |

OTHER PUBLICATIONS

Kholmanskii, "Kinetics of Photochromic Transformations", Khim. Vys. Enorg. 9(5), 4734, 1975.
Galbershtan, "Synthesis and Spectral . . . ", Khim Geterotsikl. Soedin, 1976, No. 6, 815–816.
Chu, "Photochromism of Spiroindolinonaph Thoxazine I", Can. J. Chem, 61, 1983, pp. 300–305.
*Techniques of Chemistry*, vol. III, Photochromism Glenn H. Brown, Editor, 1971, pp. 48–55, 98–105.
Platonova, "Study of the Photochromic", Zh. Fiz. Khim 54(3), 799, 1980.
Kholmanskii, "Mechanism of Intramolecular", Dokl. Akad. Nauk. SSSR, 239(4), 908–11, [Phys. Chem.], 1978.

*Primary Examiner*—Matthew A. Thexton
*Assistant Examiner*—Richard Treanor
*Attorney, Agent, or Firm*—Irwin M. Stein

[57] ABSTRACT

Described are spiro (benzidoline) pyrido benzoxazine and spiro (benzindoline) naphthoxazine photochromic compounds and their use in plastic hosts to impact a photochromic response thereto.

24 Claims, No Drawings

PHOTOCHROMIC COMPOUND AND ARTICLES CONTAINING THE SAME

This application is a continuation of application Ser. No. 07/078,325, filed July 27, 1987 now abandoned.

DESCRIPTION OF THE INVENTION

The present invention relates to novel photochromic compounds, and to compositions and articles containing such photochromic compounds. Photochromism is reversible phenomenon illustrated by a compound which, when exposed to the radiation of light involving ultraviolet rays, such as sunlight or the light of a mercury lamp, changes color and then returns to its original color if the radiation is discontinued or the compound is stored in the dark.

Various types of photochromic compounds have been synthesized and suggested for use in applications in which a color change or darkening is induced by sunlight. In particular, spiro(indoline) naphthoxazine compounds, as described in U.S. Pat. Nos. 3,562,172, 3,578,602, 4,215,010, 4,342,668, and UK patent application No. 2,171,404 are reported to be useful for sunglasses and ophthalmic lenses. Other photochromic compounds reported to be useful in ophthalmic applications are the spiro(indoline) pyrido benzoxazines, which are described in U.S. Pat. No. 4,637,698. Such photochromic compounds either in crystalline form, or in solution or dispersion in a transparent medium change rapidly from a colorless state to blue when exposed to sunlight or ultraviolet radiation and return to the original colorless state by being allowed to stand in the dark or in the absence of strong ultraviolet radiation.

DETAILED DESCRIPTION OF THE INVENTION

In accordance with the present invention, there is provided novel spiro(benzindoline) pyrido benzoxazine and spiro(benzindoline) naphthoxazine photochromic compounds, which may be represented by the following graphic formula I,

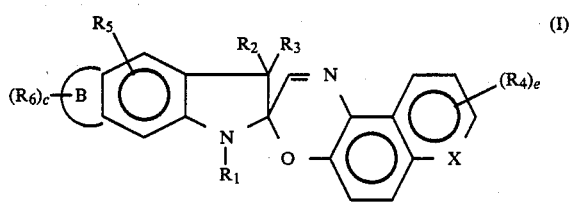

Ring B represents a substituted or unsubstituted benzene ring fused to the six membered ring of the indoline portion of the depicted formula. Ring B may be fused at the e, f, or g face of the indoline portion of the compound. Preferably, ring B is fused at the e or g face, as represented respectively by graphic formulae IA and IB:

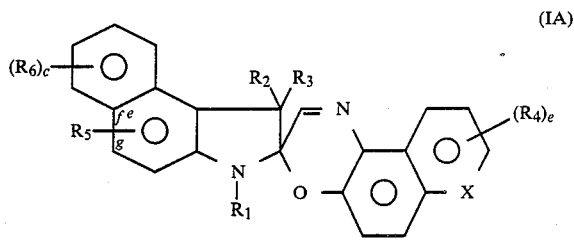

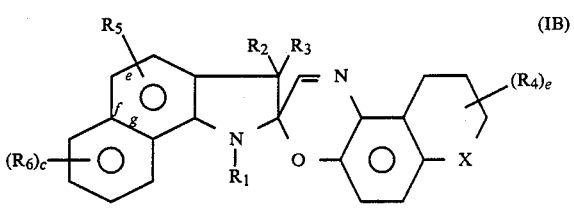

When ring B is fused at the e face, the compounds are numbered as depicted in graphic formula IA'. When ring B is fused at the g face, the compounds are numbered as depicted in graphic formula IB'.

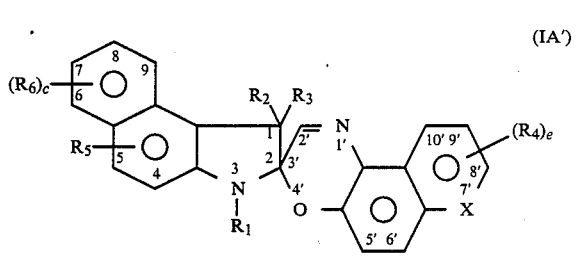

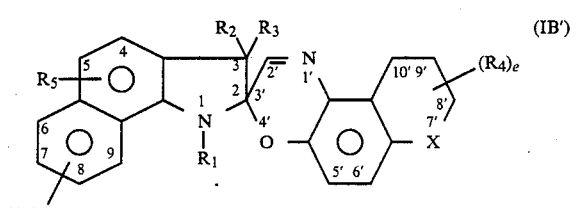

In the above graphic formulae, X is carbon or nitrogen, $R_1$ is selected from the group consisting of $C_1$–$C_8$ alkyl, e.g., methyl, ethyl, propyl, butyl, etc., phen(-$C_1$–$C_4$)alkyl, e.g., benzyl, allyl, acrylyl, methacrylyl, carboxy ($C_2$–$C_6$) alkyl, e.g., $\beta$-carboxyethyl, $\gamma$-carboxypropyl and $\delta$-carboxybutyl, cyano ($C_2$–$C_6$) alkyl, e.g., $\beta$-cyanoethyl, $\gamma$-cyanopropyl, $\beta$-cyanoisopropyl and $\delta$-cyanobutyl, $C_1$–$C_4$ acyloxy ($C_2$–$C_6$) alkyl, i.e., [$R_cC(O)R_d$—, wherein $R_c$ is a $C_1$–$C_4$ alkyl and $R_d$ is a $C_2$–$C_6$ alkyl], e.g., acetoxyethyl, acetoxypropyl, propionyloxyethyl, acetoxybutyl and propionyloxypropyl, and hydroxy ($C_2$–$C_6$) alkyl, e.g., hydroxyethyl, hydroxypropyl and hydroxybutyl. Preferably, $R_1$ is $C_1$–$C_4$ alkyl, allyl, carboxy ($C_2$–$C_4$) alkyl, cyano ($C_2$–$C_4$) alkyl, $C_1$–$C_4$ acyloxy ($C_2$–$C_4$) alkyl, e.g., $C_2$–$C_4$ acyloxyethyl, and hydroxy ($C_2$–$C_4$) alkyl.

$R_2$ and $R_3$ of formula I are each selected from the group consisting of $C_1$–$C_5$ alkyl, phenyl, mono- and di-substituted phenyl and phen ($C_1$–$C_4$) alkyl, e.g., benzyl, or $R_2$ and $R_3$ may combine to form an alicyclic ring containing from 6 to 8 carbon atoms (including the spiro carbon atom). The aforesaid phenyl substituents may be selected from $C_1$–$C_5$ alkyl and $C_1$–$C_5$ alkoxy radicals. More particularly, $R_2$ and $R_3$ are each selected from $C_1$–$C_5$ alkyl, e.g., methyl, ethyl, propyl, butyl, and pentyl, and phenyl. When one of $R_2$ or $R_3$ is a tertiary alkyl radical, such as tertiary butyl or tertiary amyl, the other is preferably an alkyl radical other than a tertiary alkyl radical.

When X is carbon and the $R_4$ substituent(s) is other than hydrogen, each $R_4$ substituent in graphic formula I may be selected from the group consisting of halogen, e.g., chloro, fluoro or bromo, $C_1$–$C_5$ alkyl, $C_1$–$C_5$ alkoxy, e.g., methoxy, ethoxy, propoxy, butoxy and pentoxy, nitro, cyano, thiocyano, $C_1$–$C_4$ monohaloalkyl, e.g., $C_1$–$C_4$ monochloroalkyl such as chloromethyl and chloroethyl, $C_1$–$C_2$ polyhaloalkyl, as for example trihaloalkyl such as trichloro- or trifluoroalkyl, e.g., trifluoromethyl and 1,1,1-trifluoroethyl, and mono-or dialkylamino wherein the alkyl moiety of the alkylamino group contains from 1 to 4 carbon atoms, e.g., methylamino, ethylamino, propylamino, dimethylamino and diethylamino. The letter "e" in formula I is an integer of from 0 to 2, e.g., 1 and denotes the number of non-hydrogen substituents. In particular, each $R_4$ substituent may be selected from the group $C_1$–$C_2$ alkyl, $C_1$–$C_2$ alkoxy, chloro, fluoro, bromo, nitro, and trifluoromethyl when e is 1 or 2.

When X is carbon and "e" is 1, the $R_4$ substituent may be located on any of the available carbon atoms of the naphtho moiety of the naphthoxazine portion of the compound, i.e., at the 5', 6', 7', 8', 9' or 10' positions. Preferably, the $R_4$ substituent is present on the 7', 8' or 9' carbon atoms. When "e" is 2, the $R_4$ substituents may be the same or different and, in either case, are selected from the above-described group. When "e" is 2, the $R_4$ substituents are commonly located at the 7' and 9' or 8' and 10' positions.

When X is nitrogen and the $R_4$ substituent(s) is other than hydrogen, each $R_4$ substituent may be selected from $C_1$–$C_5$ alkyl, e.g., $C_1$–$C_2$ alkyl, $C_1$–$C_5$ alkoxy, e.g., $C_1$–$C_2$ alkoxy, and halogen, e.g., chloro, fluoro or bromo. Typically, e is 0 (zero) when X is nitrogen and thus there are no non-hydrogen substituents. When "e" is 1 and X is nitrogen, the $R_4$ substituent may be located on any of the available carbon atoms of the pyridobenz moiety of the pyridobenzoxazine portion of the compound, i.e., at the 5', 6', 8', 9' or 10' positions, more usually at the 8', 9' or 10' positions. When "e" is 2, the $R_4$ substituent may be the same or different and, in either case, are selected from the above-described group and are located at two of aforedescribed available carbon atoms.

$R_5$ in graphic formula I is selected from the group consisting of hydrogen, halogen, e.g., chloro, fluoro or bromo, $C_1$–$C_5$ alkyl, e.g., $C_1$–$C_2$ alkyl, $C_1$–$C_5$ alkoxy, e.g., $C_1$–$C_2$ alkoxy, $C_1$–$C_4$ monohaloalkyl, e.g., $C_1$–$C_2$ monohaloalkyl such as chloromethyl, chloroethyl and fluoromethyl, $C_1$–$C_2$ polyhaloalkyl, as for example trihaloalkyl such as trichloro- or trifluoro-alkyl, e.g., trifluoromethyl, cyano and $C_1$–$C_8$ alkoxycarbonyl. The $R_5$ substituent may be located at either the number 4 or 5 carbon atom positions.

$R_6$ in graphic formula I is selected from the group consisting of halogen, e.g., chloro, fluoro or bromo, $C_1$–$C_5$ alkyl, e.g., $C_1$–$C_2$ alkyl, $C_1$–$C_5$ alkoxy, e.g., $C_1$–$C_2$ alkoxy, cyano, $C_1$–$C_8$ alkoxycarbonyl, $C_1$–$C_2$ polyhaloalkyl, $C_1$–$C_4$ monohaloalkyl or mono- or dialkylamino wherein the alkyl moiety of the alkylamino group contains from 1 to 4 carbon atoms, e.g., methylamino, ethylamino, propylamino and diethylamino.

The letter "c" in formula I is an integer of from 0 to 2, e.g. 0 or 1, more typically 0. When there are substituents on the benz moiety of the benzindoline portion of the compound and the letter "c" is 1 or 2, it denotes the number of non-hydrogen substituents. When "c" is 1, the $R_6$ substituent may be located at the number 6, 7 or 8 carbon atoms. Similarly, when "c" is 2, the $R_6$ substituents may be present at the 6 and 7, 6 and 8, or 7 and 8 carbon atoms.

Of particular interest, are photochromic materials represented by graphic formulae IA and IB wherein X is N; $R_1$ is a $C_1$–$C_4$ alkyl, such as methyl, ethyl, n-propyl, isopropyl, n-butyl, secondary butyl, isobutyl and tertiary butyl; $R_2$ and $R_3$ are each methyl, ethyl or phenyl; $R_4$ is selected from $C_1$–$C_4$ alkyl, $C_1$–$C_4$ alkoxy, chloro, fluoro or cyano; $R_5$ is selected from hydrogen, fluoro, trifluoromethyl and $C_1$–$C_4$ alkyl; $R_6$ is selected from $C_1$–$C_4$ alkyl, $C_1$–$C_4$ alkoxy, chloro, fluoro and $C_1$–$C_4$ mono- or di-alkylamino; "c" is 0 or 1; and "e" is 0 or 1.

Examples of contemplated compounds within the scope of graphic formulae IA and IB are listed in Tables I and II. In Table I, X is carbon. In Table II, X is nitrogen. The prime (') designations for the $R_4$ substituent positions in Tables I and II have been omitted. Compound 1 of Table I may be named: 9'-methoxy-1,1,3-trimethylspiro [benz[e] indoline-2,3'[3H] naphth [2,1-b][1,4] oxazine]. Usually, the $R_4$ substituent (when "e" is 1) will be located at the 8' or 9' carbon atom, more usually at the 9' carbon atom. When 'e' is 2 X is carbon, the $R_4$ substituents will usually be located at the 7' and 9' carbon atoms. For example, in Table I, the recited methoxy (OMe) and ethoxy (OEt) substituents will commonly be a 9'-methoxy or 9'-ethoxy substituent. The dimethoxy substituents of compound 13 will commonly be 7', 9'-dimethoxy substituents. The bromo substituent of compound 25 may be an 8'-bromo substituent. Compounds in Tables I and II may be similarly named as substituted spiro benz(indoline) naphthoxazines or spiro benz(indoline) pyrido benzoxazines using the substituents described in the Tables for such compounds. In naming compounds herein, the IUPAC rules of organic nomenclature have been used. Carbon atom numbering in the compounds is in accordance with the numbering sequence illustrated in graphic formulae IA' and IB'.

TABLE I

| Compound No. | SUBSTITUENT (X = C) | | | | | | |
|---|---|---|---|---|---|---|---|
| | $R_1$ | $R_2$ | $R_3$ | $R_4$ | $R_5$ | $R_6$ | Face |
| 1 | Me | Me | Me | OMe | H | — | e |
| 2 | Me | Me | Me | OMe | H | — | g |
| 3 | Et | Me | Me | OMe | H | — | e |
| 4 | n-Pr | Me | Me | OMe | H | — | e |
| 5 | i-Pr | Me | Me | OMe | H | — | e |
| 6 | Et | Me | Me | OMe | H | — | g |
| 7 | n-Pr | Me | Me | OMe | H | — | g |
| 8 | Me | Me | Me | OMe | F | — | e |

TABLE I-continued

SUBSTITUENT (X = C)

| Compound No. | R₁ | R₂ | R₃ | R₄ | R₅ | R₆ | Face |
|---|---|---|---|---|---|---|---|
| 9 | Me | Me | Me | OMe | CF₃ | — | e |
| 10 | Me | Me | Me | OMe | F | — | g |
| 11 | Me | Me | Me | OMe | CF₃ | — | g |
| 12 | Me | Me | Ph | OMe | H | Cl | g |
| 13 | Me | Me | Me | (OMe)₂ | OMe | — | g |
| 14 | Et | Me | Me | NEt₂ | H | OMe | e |
| 15 | Me | Me | Me | OMe | Me | Me | g |
| 16 | Me | Me | Me | Me | Me | Me | e |
| 17 | Me | Me | Me | NO₂ | CF₃ | — | g |
| 18 | Me | Me | Me | Cl | H | — | e |
| 19 | i-Pr | Me | Me | CF₃ | H | — | e |
| 20 | Me | Me | Me | ClMe | CF₃ | — | g |
| 21 | Me | Me | Me | OMe | AcO | — | g |
| 22 | Me | Me | Me | OMe | ClMe | Cl | e |
| 23 | Me | Me | Me | — | H | — | e or g |
| 24 | Me | Me | Me | OEt | H | — | e or g |
| 25 | Me | Me | Me | Br | H | — | e or g |
| 26 | (CH₂)₃CN | Me | Me | OMe | H | — | e or g |
| 27 | (CH₂)COOH | Me | Me | OMe | H | — | e or g |
| 28 | (CH₂)₂OH | Me | Me | OMe | H | — | e or g |

TABLE II

SUBSTITUENT (X = N)

| Compound No. | R₁ | R₂ | R₃ | R₄ | R₅ | R₆ | Face |
|---|---|---|---|---|---|---|---|
| 1 | Me | Me | Me | H | H | — | e |
| 2 | Me | Me | H | H | H | — | g |
| 3 | Me | Me | Me | Me | H | — | e or g |
| 4 | Me | Me | Me | OMe | H | — | e or g |
| 5 | Me | Me | Me | Cl | H | — | e or g |
| 6 | Me | Me | Me | — | F | — | e or g |
| 7 | Me | Me | Me | — | CF₃ | — | e or g |
| 8 | Et | Me | Me | — | H | — | e or g |
| 9 | n-Pr | Me | Me | — | H | — | e or g |
| 10 | i-Pr | Me | Me | — | H | — | e |
| 11 | Me | Me | Et | Me | CF₃ | F | g |
| 12 | Me | Me | Me | OMe | Me | Me | g |
| 13 | Me | Me | Et | OMe | H | OMe | g |
| 14 | Me | Me | Me | OMe | F | NEt₂ | g |
| 15 | Me | Me | Et | F | F | Me | g |
| 16 | Me | Me | Me | Me | H | — | e or g |
| 17 | (CH₂)₃CN | Me | Me | — | H | — | e or g |
| 18 | (CH₂)₂COOH | Me | Me | — | H | — | e or g |
| 19 | (CH₂)₂OH | Me | Me | — | H | — | e or g |
| 20 | Me | Me | Me | — | H | CF₃ | e or g |
| 21 | Me | Me | Me | — | H | F | e or g |

Key For Tables:
Me = methyl
Et = ethyl
n-Pr = n-propyl
i-Pr = isopropyl
(CH₂)₃CN = cyanopropyl
(CH₂)₂COOH = carboxyethyl
Ph = phenyl
OMe = methoxy
NO₂ = nitro
NEt₂ = diethylamino
(CH₂)₂OH = hydroxyethyl
CF₃ = trifluoromethyl
ClMe = chloromethyl
Cl = chlorine
F = fluorine
AcO = acetoxy
A hyphen (-) denotes the absence of non-hydrogen substituents Compound 1 of Table I may be graphically represented by the following formula:

Compound 2 of Table I may be graphically represented by the following formula:

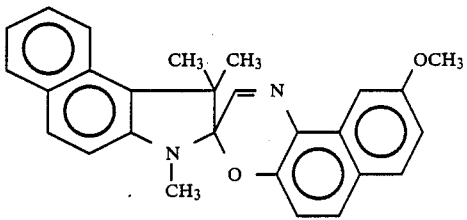

Compound 1 of Table II may be graphically represented by the following formula:

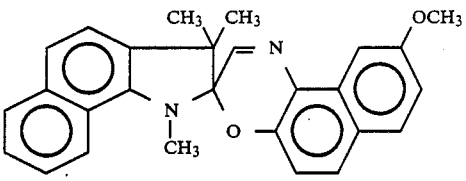

Compound 2 of Table II may be graphically represented by the following formula:

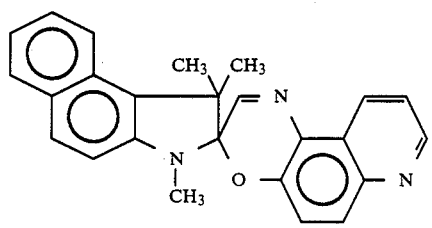

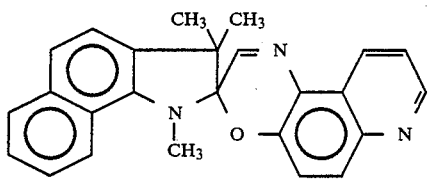

The photochromic materials of the present invention may be synthesized by reaction of the corresponding $R_5$ and $(R_6)_c$-substituted indoline (Fischer's base) or indolium salt, e.g., the iodide salt, with the corresponding $(R_4)_e$-substituted-1-nitroso-2-naphthol or $(R_4)_e$-substituted-5-nitroso-6-quinolinol.

The two precursor materials are reacted in substantially stoichiometric amounts in a suitable solvent, such as toluene or ethanol, containing a base, such as triethylamine or piperidine, (when the indolium salt is used) at temperatures of from about 40° C. to about 140° C., more usually from 40° C. to 120° C., until the reaction is completed.

Any common organic solvent (polar and non-polar) except for low boiling aliphatic hydrocarbon solvents, such as pentane, may be used as the reaction medium. Contemplated as suitable solvents are alcohols such as $C_1$–$C_4$ alkanols, e.g., methanol, ethanol, isopropanol, and the butanols; aromatic solvents such as benzene, toluene and xylene; ketones such as acetone, methyl ethyl ketone and methyl isobutyl ketone; esters such as ethyl acetate; chlorinated lower aliphatic hydrocarbons such as methylene chloride and chloroform; dimethylsulfoxide, dimethylformamide tetrahydrofuran; and mixtures of $C_1$–$C_4$ alkanols and aliphatic hydrocarbon solvents such as ethanol-hexane and ethanol-heptane mixtures.

While reaction temperatures below 40° C. may be used, the reaction rate is very slow and inefficient. Reaction temperature above 120° C. may cause decomposition of the product. Hence, temperatures of from 40° C. to 120° C., e.g., 50° C. to 100° C. are considered most suitable. Stirring of the reaction medium at elevated reaction temperature within the aforesaid ranges is recommended to prevent decomposition of the product.

An organic or inorganic base may be used to react with the hydrogen halide that is liberated during the reaction as a result of using an indolium halide salt reactant. Amines such as trimethylamine, triethylamine, diisopropylamine, piperidine, pyridine and piperazine may be used. Inorganic basic reagents such as sodium carbonate, sodium bicarbonate, potassium hydroxide, sodium hydroxide and sodium acetate may be used. The use of inorganic reagents will entail a two-phase reaction medium, i.e., an inorganic and organic phase. The basic reagent is commonly used in a stoichiometric excess, although stoichiometric amounts may be used.

The photochromic material is recovered from the reaction mixture, e.g., by filtration or decanting—depending on whether the product is a solid or liquid. The product may be purified by flash column chromatography, crystallization, boiling with carbon black or other techniques known in the art.

More particularly, the photochromic compounds of the present invention may be prepared by reacting one equivalent of the corresponding substituted Fischer's base hydroiodide salt with one equivalent of the corresponding substituted nitrosonaphthol or nitrosoquinolinol in an ethanol solution containing an excess of triethylamine. The liquid reaction mixture is heated to 70° C. and maintained at about that temperature for about 5 hours. The progress of the reaction may be monitored by thin layer chromatography (TLC). The ethanol solvent and excess triethylamine are evaporated and the residue purified by column chromatography using ethylacetate and hexane as eluents, or by recrystallization from appropriate solvents.

Still more particularly, one equivalent of 7-methoxy-1-nitroso-2-naphthol may be condensed with an equivalent of 1,2,3,3-tetramethyl benz(g) indoline. A suspension of the iodide salt and the nitroso-2-naphthol in a hexane/ethanol mixture may be refluxed under nitrogen until the condensation reaction has been completed, e.g., 2 to 6 hours. The resulting spiro benz[g] (indoline) naphthoxazine, i.e., 9'-methoxy-1,3,3-trimethylspiro[benz[g] indoline-2,3'- [3H] naphth [2,1-b] [1,4] oxazine], is compound 2 in Table I.

The $(R_6)_c$-substituted indoline (or indolium salt) may be prepared by converting the corresponding $R_5$- and $(R_6)_c$-substituted naphthylamine to the corresponding hydrazine hydrochloride by conventional synthesis procedures. See, for example. R. K. Brown, "The Chemistry of Heterocyclic Compounds", Wiley Interscience, New York, Volume 25, Part I, Chapter 2, page 232.

The hydrazine hydrochloride may be condensed with the required ketone by reaction of stoichiometric amounts of the reagents in glacial acetic acid at 100° C. or in refluxing ethanol to form the corresponding (3H)indole. The (3H)indole may be converted to the Fischer's base hydroiodide salt by alkylation with excess methyl iodide under reflux conditions.

The photochromic materials in the present invention may be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. The compounds can also be dispersed in liquids containing water, alcohols and other solvents.

The photochromic materials of the present invention may also be dissolved in colorless or transparent solutions prepared from transparent organic host materials, e.g., transparent polymers (or copolymers) or blends of such transparent polymers and optionally a suitable organic solvent, e.g., polymers of transparent organic host materials described hereinafter dissolved in one or more of the aforesaid described organic solvents. Examples of such solutions include a polyvinyl-acetate-acetone solution, a nitrocellulose-acetonitrile solution, a polyvinyl-chloride-methylethylketone solution, a polymethylmethacrylate acetone solution, a cellulose acetate-dimethylformamide solution, a polyvinyl-pyrrolidone-acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate and polyethylene terephthalate, or baryta paper and dried to obtain an article that may be color formed by ultraviolet radiation and returned to colorless by removing the source of ultraviolet radiation.

In an embodiment of the present invention, the photochromic materials described herein (or compositions containing them) may be applied to or incorporated within a coating composition applied to a compatible support; or applied to or incorporated within the article comprising the compatible host, e.g., a polymerized organic material such as a synthetic plastic host material. Preferably, the host material article is a solid transparent material or an optically clear material, e.g., materials suitable for ophtalmic elements, such as ophthalmic lenses, or materials useful for applications such as windows, windshields, etc. A host material containing the photochromic compounds of the present invention can be used in the preparation of photochromic plastic films, sheets and lenses, such as lenses for sunglasses, ski goggles, visors, camera lenses and variable density filters. As used herein, the term "optical element" is meant to include lenses and transparencies. The photochromic materials of the present invention also may be incorporated into coatings such as paints, inks, etc. by admixing the material with the fluid coating composition before it is applied to the host surface and dried.

Examples of host materials which can be used with the photochromic compounds of the present invention include: polymers e.g., homopolymers and copolymers of polyol(allyl carbonate) monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, polyethyleneterephthalate, polystyrene, poly(styrene-methylmethacrylate) copolymers, poly(styrene-acrylonitrile) copolymer, and polyvinylbutyral. Transparent copolymers and blends of the transparent polymers are also suitable as host materials. Preferably, the host material is an optically clear polymerized organic material prepared from a polycarbonate, such as poly(4,4'-dioxydiphenol-2,2-propane), which is sold under the trademark, LEXAN; a polymethylmethacrylate, such as the material sold under the trademark, PLEXIGLAS; polymerizates of a polyol(allyl carbonate), especially diethylene glycol bis(allyl carbonate), which is sold under the trademark CR-39, and its copolymers with for example vinyl acetate, e.g., copolymers of from 80-90 percent diethylene glycol bis(allyl carbonate) and 10-20 percent vinyl acetate; particularly 80-85 percent of the bis(allyl carbonate) and 15-20 percent vinyl acetate, cellulose acetate, cellulose propionate, cellulose butyrate, polystyrene and its copolymers with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The polyol (allyl carbonate) monomers can be represented by the graphic formula:

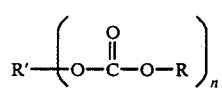

(II)

wherein R is the radical derived from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

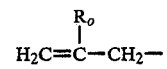

wherein $R_o$ is hydrogen, halogen, or a $C_1$-$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly R is the allyl group, $H_2C\!=\!CH\!-\!CH_2\!-\!$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

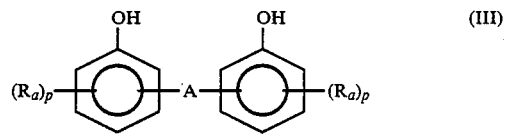

(III)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene:), Ra represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2C-H_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(para-phenyl),

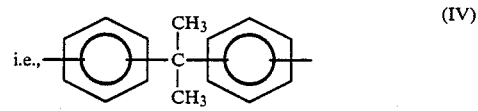

(IV)

Most commonly, R' is —CH$_2$CH$_2$—, —CH$_2$CH$_2$—O—CH$_2$CH$_2$—, or —CH$_2$CH$_2$—O—CH$_2$CH$_2$—O—CH$_2$Ch$_2$—.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis (allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis (allyl carbonate).

Industrially important polyol bis (allyl carbonate) monomers which can be utilized in the invention herein contemplated are:

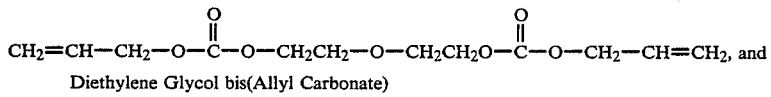
Triethylene Glycol bis(Allyl Carbonate)        (V)

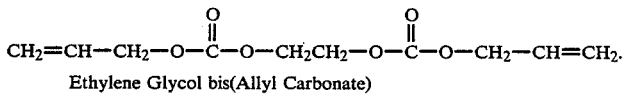
Diethylene Glycol bis(Allyl Carbonate)         (VI)

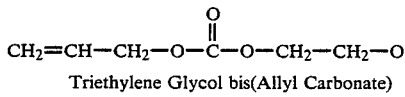
Ethylene Glycol bis(Allyl Carbonate)           (VII)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

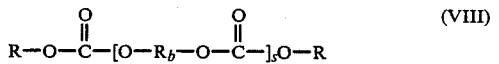                                (VIII)

wherein R is as defined above, R$_b$ is a bivalent radical, e.g., alkylene or phenylene, derived from a diol, and s is a whole number from 2 to 5. The related monomer species of diethylene glycol bis(allyl carbonate) can be represented by the graphic formula,

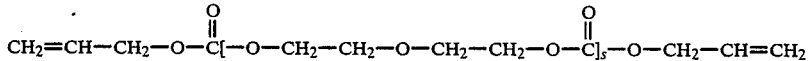                                (IX)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis-(allyl carbonate), are intended to mean and include the named monomer or prepolymer and any related monomer species contained therein.

The amount of photochromic compound or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic compound. Typically, the more compound applied or incorporated, the greater is the color intensity. Usually, the amount of photochromic compound incorporated into or applied to the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 50, e.g., 1 to 10 milligrams of the photochromic compound per square inch of the surface of the host material independent of the thickness of the host material article. Hence, the photochromic compound is present in higher concentrations in thin samples, films, or coatings, and in lower concentrations in thick samples.

Solutions of the photochromic compounds of the present invention undergo a change in color upon exposure to ultraviolet radiation and return to their original color or colorless state upon removal of the source of ultraviolet radiation. Such color change may be repeated numerous times.

The photochromic compounds (or compositions containing same) of the present invention can be applied to or incorporated into a host material by methods known in the art. Such methods include dissolving or dispersing the compound in the host material, i.e., imbibation of the photochromic compound into the host material, by immersion, thermal transfer, or coating, and incorporation of the photochromic compound as part of a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds (or compositions containing same) of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in water, alcohol or other solvents or solvent mixtures and then imbided into the solid host material by immersion for from several minutes to several hours, e.g., 2-3 minutes to 2-3 hours of the host material in a bath of such solution or dispersion. The bath is conventionally at an elevated temperature, usually in the range of 50° C.-120° C. Thereafter, the host material is removed from the bath and dried;

(c) The photochromic compounds (and compositions containing same) may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g., in an oven, for from a minute to several hours at temperatures in the range of from 80°-180° C.;

(d) In a variation of the above imbibation procedure, the photochromic compound or composition containing same can be deposited onto a temporary support, e.g., a sheet of kraft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of a permanent adherent film or coating by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of a host material(s).

The present invention is more particularly described in the following examples which are intended as illustrative only since numerous modifications and variations therein will be apparent to those skilled in the art.

EXAMPLE 1

To a solution of 1.05 grams (3.0 mmole) of 1,2,3,3-tetramethyl-3H-benz[g] indolium iodide in 15 milliliters (ml) of hexane at 25° C. was added 10 ml (50 mmole) of 20% sodium hydroxide. The two phase mixture was stirred vigorously under nitrogen for about 30 minutes. The organic layer was separated, transferred to a reaction flask equipped with a reflux condenser and diluted with 15 ml of absolute ethanol. To this solution was added 0.61 grams (3.0 mmole) of 7-methoxy-1-nitroso-2-naphthol and the resulting reaction mixture refluxed under nitrogen for about 6 hours. The reaction mixture was cooled, the volume reduced under vacuum and 0.29 grams (0.71 mmole) of the product, 9'-methoxy-1,3,3-trimethylspiro [benz[g] indoline-2,3'-[3H] naphth [2,1-b][1,4] oxazine] was obtained as yellow-orange crystals. A solution of the crystals dissolved in ethanol or toluene was colorless. The solution turned blue when irradiated with ultraviolet light.

EXAMPLE 2

To a solution of 1.05 grams (3.0 mmole) of 1,2,3,3-tetramethyl-3H-benz[e] indolium iodide in 15 ml of absolute ethanol under nitrogen was added 0.56 ml of triethylamine (4 mmole) and 20 ml of hexane. The solution was heated to 50° C. and 0.61 grams (3.0 mmole) of 7-methoxy-1-nitroso-2-naphthol added over about 10 minutes. The resulting solution was deep red. The solution was heated to and maintained at 60°-65° C. for 3 hours and then permitted to cool overnight. The volume of the cooled reaction mixture was reduced under vacuum and a grey solid recovered by filtration. The solid product was recrystallized from a 50/50 ethanol/hexane mixture to obtain 0.70 grams (1.72 mmole) of the product, 9'-methoxy-1,1,3-trimethylspiro [benz[e] indoline-2,3'-[3H] naphth [2,1-b][1,4] oxazine] as a grey-green solid. A solution of the solid in ethanol or toluene was colorless, but turned blue when irradiated with ultraviolet light.

EXAMPLE 3

The procedure of Example 2 was followed using 0.52 grams (3.0 mmole) of 5-nitroso-6-quinolinol in place of the 7-methoxy-1-nitroso-2-naphthol. The reaction mixture was heated at about 55° C. for about three hours, cooled and the solvent removed. The product residue was treated three times with 20 ml of hexane. The hexane solutions were combined, and the solution volume reduced under vacuum. The residue was recrystallized from hexane:ethanol (ca. 9:1) to yield 0.18 grams (0.05 mmole) of the yellow-green solid product, 1,1,3-trimethylspiro [benz[e] indoline-2,3'-[3H] pyrido [3,2-f][1,4] benzoxazine]. A solution of the product in ethanol or toluene was colorless; but, turned blue when irradiated with ultraviolet light.

EXAMPLE 4

To a solution of 3.51 grams (10 mmoles) of 1,2,3,3-tetramethyl-3H benz[g] indolium iodide in 50 ml of ethanol was added 2.1 ml (15 mmole) of trethylamine. The solution was heated to about 65° C. and 2.18 grams (10 mmole) of 5-nitroso-6-quinolinol was added to the solution over about 30 minutes. The resulting reaction mixture was heated under reflux for 3 hours and allowed to cool overnight with stirring. The solvent was removed under vacuum and the residue purified by flash chromatography to yield 0.33 grams of the yellow solid product, 1,3,3-trimethylspiro [benz[g] indoline-2,3'-[3H] pyrido [3,2-f][1,4] benzoxazine]. A solution of the product in ethanol or toluene was colorless; but, turned blue when irradiated with ultraviolet light.

Although the present invention has been described with reference to specific details of certain embodiments thereof, it is not intended that such detail should be regarded as limitations upon the scope of the invention except as and to the extent that they are included in the accompanying claims.

We claim:

1. A compound represented by the following graphic formula:

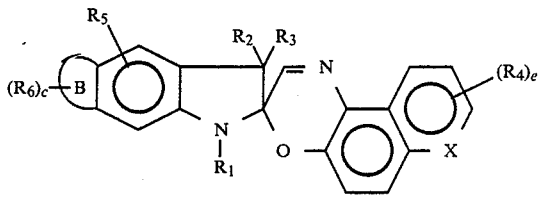

wherein:
(a) B is a benzene ring fused at the e or g face and X is carbon or nitrogen;
(b) $R_1$ is selected from the group consisting of $C_1$–$C_8$ alkyl, phen ($C_1$–$C_4$) alkyl, allyl, acrylyl, methacrylyl, carboxy ($C_2$–$C_6$) alkyl, cyano ($C_2$–$C_6$) alkyl, hydroxy ($C_2$–$C_6$) alkyl, and ($C_1$–$C_4$) acyloxy ($C_2$–$C_6$) alkyl;
(c) $R_2$ and $R_3$ are each selected from the group consisting of $C_1$–$C_5$ alkyl, phenyl, mono- and di- substituted phenyl, and phen ($C_1$–$C_4$) alkyl, or combine to form an alicyclic ring containing from 6 to 8 carbon atoms (including the spiro carbon atom), said phenyl substituents being selected from $C_1$–$C_5$ alkyl and $C_1$–$C_5$ alkoxy;
(d) each $R_4$ is selected from the group consisting of halogen, $C_1$–$C_5$ alkyl, $C_1$–$C_5$ alkoxy, nitro, cyano, thiocyano, $C_1$–$C_4$ monohaloalkyl, $C_1$–$C_2$ polyhaloalkyl, and mono- and di($C_1$–$C_4$) alkylamino when X is carbon; and is selected from the group consisting of $C_1$–$C_5$ alkyl, $C_1$–$C_5$ alkoxy and halogen when X is nitrogen;
(e) $R_5$ is selected from the group consisting of hydrogen, halogen, $C_1$–$C_5$ alkyl, $C_1$–$C_5$ alkoxy, $C_1$–$C_4$ monohaloalkyl, $C_1$–$C_2$ polyhaloalkyl, cyano and $C_1$–$C_8$ alkoxycarbonyl;
(f) each $R_6$ is selected from the group consisting of halogen, $C_1$–$C_5$ alkyl, $C_1$–$C_5$ alkoxy, cyano, $C_1$–$C_8$ alkoxycarbonyl, $C_1$–$C_4$ monohaloalkyl, $C_1$–$C_2$ polyhaloalkyl, and mono- or di($C_1$–$C_4$) alkylamino; and
(g) e and c are each integers of from 0 to 2.

2. A compound of claim 1 wherein X is carbon; $R_1$ is $C_1$–$C_4$ alkyl, allyl, carboxy ($C_2$–$C_4$) alkyl, cyano ($C_2$–$C_4$) alkyl, $C_1$–$C_4$ acyloxy ($C_2$–$C_4$) alkyl, or hydroxy ($C_2$–$C_4$) alkyl; $R_2$ and $R_3$ are each $C_1$–$C_5$ alkyl or phenyl; each $R_4$ is $C_1$–$C_2$ alkyl, $C_1$–$C_2$ alkoxy, chloro, fluoro, bromo, nitro or trifluoromethyl; $R_5$ is hydrogen, fluoro, trifluoromethyl, or $C_1$–$C_4$ alkyl, $R_6$ is fluoro, trifluoromethyl, $C_1$–$C_2$ alkyl or $C_1$–$C_2$ alkoxy; e is 0 to 2, and c is 0 to 1.

3. A compound of claim 2 wherein $R_1$ is $C_1$–$C_2$ alkyl, allyl or cyano $C_2$–$C_4$ alkyl, $R_2$ and $R_3$ are each $C_1$–$C_5$ alkyl, each $R_4$ is $C_1$–$C_2$ alkyl, $C_1$–$C_2$ alkoxy, chloro or fluoro, $R_5$ is hydrogen, c is 0 and e is 0 to 2.

4. A compound of claim 1 wherein X is nitrogen, $R_1$ is $C_1$–$C_4$ alkyl, allyl, carboxy ($C_2$–$C_4$) alkyl, cyano $C_2$–$C_4$ alkyl, $C_1$–$C_4$ acyloxy ($C_2$–$C_4$) alkyl, or hydroxy ($C_2$–$C_4$) alkyl; $R_2$ and $R_3$ are each $C_1$–$C_5$ alkyl or phenyl; each $R_4$ is $C_1$–$C_2$ alkyl, $C_1$–$C_2$ alkoxy, chloro, fluoro, or bromo; $R_5$ is hydrogen, fluoro, trifluoromethyl or $C_1$–$C_4$ alkyl; $R_6$ is fluoro, trifluoromethyl, $C_1$–$C_2$ alkyl or $C_1$–$C_2$ alkoxy; e is 0 to 2, and c is 0 or 1.

5. A compound of claim 4 wherein $R_1$ is $C_1$–$C_4$ alkyl, allyl or cyano $C_2$–$C_4$ alkyl, $R_2$ and $R_3$ are each $C_1$–$C_5$ alkyl, each $R_4$ is $C_1$–$C_2$ alkyl, $C_1$–$C_2$ alkoxy, chloro or fluoro, $R_5$ is hydrogen, c is 0 and e is 0 to 2.

6. The compound, 9′-methoxy-1,1,3-trimethylspiro[benz[e] indoline-2,3′[3H] naphth [2,1-b][1,4] oxazine].

7. The compound, 9′-methoxy-1,3,3-trimethylspiro [benz[g] indoline-2,3′[3H] naphth [2,1-b][1,4] oxazine].

8. The compound, 1,1,3-trimethylspiro [benz[e] indoline-2,3′-[3H] pyrido [3,2-f][1,4] benzoxazine].

9. The compound, 1,3,3-trimethylspiro [benz[g] indoline-2,3′-[3H] pyrido [3,2-f][1,4] benzoxazine].

10. A photochromic composition comprising a transparent organic host material containing a photochromic amount of a photochromic compound represented by the graphic formula:

(a) B is a benzene ring fused at the e or g face and X is carbon or nitrogen;
(b) $R_1$ is selected from the group consisting of $C_1$–$C_8$ alkyl, phen ($C_1$–$C_4$) alkyl, allyl, acrylyl, methacrylyl, carboxy ($C_2$–$C_6$) alkyl, cyano ($C_2$–$C_6$) alkyl, hydroxy $C_2$–$C_6$ alkyl, and ($C_1$–$C_4$) acyloxy ($C_2$–$C_6$) alkyl;
(c) $R_2$ and $R_3$ are each selected from the group consisting of $C_1$–$C_5$ alkyl, phenyl, mono- and di- substituted phenyl, and phen ($C_1$–$C_4$) alkyl, or combine to form an alicyclic ring containing from 6 to 8 carbon atoms (including the spiro carbon atom), said phenyl substituents being selected from $C_1$–$C_5$ alkyl and $C_1$–$C_5$ alkoxy;
(d) each $R_4$ is selected from the group consisting of halogen, $C_1$–$C_5$ alkyl, $C_1$–$C_5$ alkoxy, nitro, cyano, thiocyano, $C_1$–$C_4$ monohaloalkyl, $C_1$–$C_2$ polyhaloalkyl, and mono- and di($C_1$–$C_4$) alkylamino when X is carbon; and is selected from the group consisting of $C_1$–$C_5$ alkyl, $C_1$–$C_5$ alkoxy and halogen when X is nitrogen;
(e) $R_5$ is selected from the group consisting of hydrogen, halogen, $C_1$–$C_5$ alkyl, $C_1$–$C_5$ alkoxy, $C_1$–$C_4$ monohaloalkyl, $C_1$–$C_2$ polyhaloalkyl, cyano and $C_1$–$C_8$ alkoxycarbonyl;
(f) each $R_6$ is selected from the group consisting of halogen, $C_1$–$C_5$ alkyl, $C_1$–$C_5$ alkoxy, cyano, $C_1$–$C_8$ alkoxycarbonyl, $C_1$–$C_4$ monohaloalkyl, $C_1$–$C_2$ polyhaloalkyl, and mono- or di($C_1$–$C_4$) alkylamino; and
(g) e and c are each integers of from 0 to 2.

11. The photochromic composition of claim 10 wherein the transparent organic host material is selected from the group consisting essentially of polymers of polyol(allyl carbonate), polyacrylates, poly(alkylacrylates), cellulose acetate, cellulose triacetate, cellulose acetate propionate, cellulose acetate butyrate, poly(vinyl acetate), poly(vinyl alcohol), polycarbonate, polystyrene, poly(styrene-methylmethacrylate) copolymers, poly(styrene-acrylonitrile) copolymers, and polyvinyl butyral.

12. The photochromic composition of claim 11 wherein the polyol(ally carbonate) polymer is selected from poly and its copolymers with vinyl acetate.

13. The photochromic composition of claim 11 wherein X is carbon; $R_1$ is $C_1$–$C_4$ alkyl, allyl, carboxy ($C_2$–$C_4$) alkyl, cyano ($C_2$–$C_4$) alkyl, $C_1$–$C_4$ acyloxy ($C_2$–$C_4$) alkyl, or hydroxy ($C_2$–$C_4$) alkyl; $R_2$ and $R_3$ are each $C_1$–$C_5$ alkyl or phenyl; each $R_4$ is $C_1$–$C_2$ alkyl, $C_1$–$C_2$ alkoxy, chloro, fluoro, bromo, nitro or trifluoromethyl; $R_5$ is hydrogen, fluoro, trifluoromethyl, or $C_1$–$C_4$ alkyl, $R_6$ is fluoro, trifluoromethyl, $C_1$–$C_2$ alkyl or $C_1$–$C_2$ alkoxy; e is 0 to 2, and c is 0 or 1.

14. The photochromic composition of claim 13 wherein ring B is fused at the e or g face of the indoline moiety.

15. The photochromic composition of claim 11 wherein X is nitrogen; $R_1$ is $C_1$–$C_4$ alkyl, allyl, carboxy ($C_2$–$C_4$) alkyl, cyano ($C_2$–$C_4$) alkyl, $C_1$–$C_4$ acyloxy ($C_2$–$C_4$) alkyl, or hydroxy ($C_2$–$C_4$) alkyl; $R_2$ and $R_3$ are each $C_1$–$C_5$ alkyl or phenyl; each $R_4$ is $C_1$–$C_2$ alkyl, $C_1$–$C_2$ alkoxy, chloro, fluoro or bromo; $R_5$ is hydrogen, fluoro, trifluoromethyl, or $C_1$–$C_4$ alkyl, $R_6$ is fluoro, trifluoromethyl, $C_1$–$C_2$ alkyl or $C_1$–$C_2$ alkoxy; e is 0 to 2, and c is 0 or 1.

16. The photochromic composition of claim 15 wherein ring B is fused at the e or g face of the indoline moiety.

17. A photochromic article comprising a solid transparent polymerized organic host material selected from the group consisting of polycarbonate, polymers of polyol(allyl carbonate), polymethylmethacrylate, cellulose acetate, cellulose propionate, cellulose butyrate, cellulose acetate butyrate, polystyrene, poly(styrene-metylmethacrylate) copolymer, and poly(styrene-acrylonitrile) copolymer, containing a photochromic amount of a photochromic compound represented by the graphic formula:

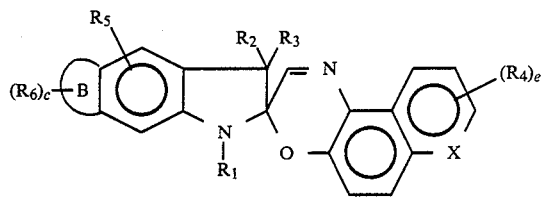

wherein:
(a) ring B is a benzene ring fused at the e or g face of the indoline moiety and X is carbon or nitrogen;
(b) $R_1$ is $C_1$–$C_4$ alkyl, cyano($C_2$–$C_4$) alkyl or allyl:
(c) $R_2$ and $R_3$ are each $C_1$–$C_5$ alkyl or phenyl;
(d) each $R_4$ is $C_1$–$C_2$ alkyl, $C_1$–$C_2$ alkoxy, chloro, fluoro, bromo, nitro or trifluoromethyl when X is carbon; and is $C_1$–$C_2$ alkyl, $C_1$–$C_2$ alkoxy, chloro, fluoro, or bromo when X is nitrogen;
(e) $R_5$ is hydrogen, fluoro, trifluoromethyl or $C_1$–$C_2$ alkyl;
(f) $R_6$ is fluoro, trifluoromethyl, $C_1$–$C_2$ alkyl, or $C_1$–$C_2$ alkoxy; and
(g) e is 0 to 2, and c is 0 to 1.

18. The photochromic article of claim 17 wherein the photochromic compound is present in amounts of from 0.05 to 10 weight percent.

19. The photochromic article of claim 18 wherein the polyol(allyl carbonate) polymer is selected from poly and its copolymers with vinyl acetate.

20. The photochromic article of claim 19 wherein the copolymer is from 80–90 percent diethylene glycol bis(allyl carbonate) and 10–20 percent vinyl acetate.

21. The photochromic article of claim 17 wherein the article is an optical element.

22. The photochromic article of claim 21 wherein the optical element is a lens.

23. The photochromic article of claim 18 wherein the host material is selected from polymers of diethylene glycol bis(allyl carbonate).

24. The photochromic article of claim 23 wherein the article is a lens.

* * * * *

UNITED STATES PATENT AND TRADEMARK OFFICE
CERTIFICATE OF CORRECTION

PATENT NO. : 4,931,219

DATED : June 5, 1990

INVENTOR(S) : Patricia L. Kwiatkowski, et al.

It is certified that error appears in the above-identified patent and that said Letters Patent is hereby corrected as shown below:

Claim 12, column 16, line 66, "poly" should be --poly[diethylene glycol bis(allyl carbonate)]--

Claim 19, column 18, line 29, "poly" should be --poly[diethylene glycol bis(allyl carbonate)]--

Signed and Sealed this

First Day of October, 1991

Attest:

Attesting Officer

HARRY F. MANBECK, JR.

Commissioner of Patents and Trademarks